United States Patent [19]

Wang et al.

[11] Patent Number: 5,274,335

[45] Date of Patent: Dec. 28, 1993

[54] OIL SENSOR SYSTEMS AND METHODS OF QUALITATIVELY DETERMINING OIL TYPE AND CONDITION

[75] Inventors: Su-Chee S. Wang, Troy; Han-Sheng Lee, Bloomfield; Phillip B. McGrath, Sterling Heights; David R. Staley, Flushing, all of Mich.

[73] Assignee: General Motors Corporation, Detroit, Mich.

[21] Appl. No.: 863,907

[22] Filed: Apr. 6, 1992

[51] Int. Cl.$^5$ .................. G01R 27/26; G01N 15/00
[52] U.S. Cl. .................. 324/689; 324/663; 73/61.43
[58] Field of Search .............. 324/663, 664, 689, 690; 73/61.41, 61.43, 61.44

[56] References Cited

U.S. PATENT DOCUMENTS

| | | | |
|---|---|---|---|
| 2,004,569 | 6/1935 | Davis, Jr. | 175/183 |
| 2,184,338 | 12/1939 | Ennis | 175/183 |
| 2,782,151 | 2/1957 | Suthard | 204/1 |
| 3,331,019 | 7/1967 | Irwin | 324/663 |
| 4,007,629 | 2/1977 | Hochstein | 73/53 |
| 4,059,406 | 11/1977 | Fleet | 23/230 R |
| 4,112,744 | 9/1978 | Tassano | 73/61.43 |
| 4,306,525 | 12/1981 | Faxvog | 123/196 S |
| 4,410,885 | 10/1983 | Stenstrom | 340/604 |
| 4,503,384 | 3/1985 | Nagy et al. | 324/61 P |
| 4,506,337 | 3/1985 | Yasuhara | 364/550 |
| 4,544,880 | 10/1985 | Nagy et al. | 324/58.5 R |
| 4,570,069 | 2/1986 | Gager | 250/343 |
| 4,629,334 | 12/1986 | Hochstein | 374/103 |
| 4,646,070 | 2/1987 | Yasuhara et al. | 340/603 |
| 4,686,857 | 8/1987 | Kato | 73/304 R |
| 4,694,793 | 9/1987 | Kawakita et al. | 123/196 S |
| 4,701,713 | 10/1987 | Eaton et al. | 324/442 |
| 4,733,556 | 3/1988 | Meitzler et al. | 73/64 |
| 4,740,777 | 4/1988 | Slocum et al. | 73/61.43 |
| 4,741,204 | 5/1988 | Luck et al. | 73/116 |
| 4,744,870 | 5/1988 | Kauffman | 204/1 T |
| 4,764,258 | 8/1988 | Kauffman | 201/1 T |
| 4,785,287 | 11/1988 | Honma et al. | 340/631 |
| 4,791,374 | 12/1988 | Yodice et al. | 324/439 |
| 4,961,064 | 10/1990 | Hara | 338/231 |
| 5,005,402 | 4/1991 | Pischinger et al. | 324/663 |
| 5,023,133 | 6/1991 | Yodice et al. | 428/332 |
| 5,067,345 | 11/1991 | Mougne | 73/61.44 |
| 5,103,184 | 4/1992 | Kapsokavathis et al. | 324/663 |

FOREIGN PATENT DOCUMENTS

| | | | |
|---|---|---|---|
| 0193343 | 11/1984 | Japan | 324/663 |
| 1187056 | 10/1985 | U.S.S.R. | 324/689 |

OTHER PUBLICATIONS

Wm. Blum et al., "Principles of Electroplating and Electroforming (Electrotyping)", Third Edition, McGraw-Hill Book Company, Inc. Dec. 1949, p. 378.
R. S. Nicholson et al., "Theory of Stationary Electrode Polarography Single Scan and Cyclic Methods Applied to reversible, Irreversible, and Kinetic Systems", Analytical Chemistry, pp. 706-723 Apr. 1964.
Takayuki Kato et al., "Oil Maintenance Tester: A New Device to Detect the Degradation Level of Oils", Lubrication Engineering, Nov. 1986, pp. 694-699.

Primary Examiner—Kenneth A. Wieder
Assistant Examiner—Maura K. Regan
Attorney, Agent, or Firm—Cary W. Brooks

[57] ABSTRACT

Disclosed is an oil sensor system having an oil sensor including two spaced apart electrodes, a triangular waveform means, a comparison means and a signal means. The oil system is used in situ (i.e., used directly in the engine) to determine the presence of two-stroke or four-stroke oil, or the occurrence of an engine malfunction, such as a leakage of antifreeze into the oil.

14 Claims, 5 Drawing Sheets

OIL SENSOR SYSTEMS AND METHODS OF QUALITATIVELY DETERMINING OIL TYPE AND CONDITION

FIELD OF THE INVENTION

The invention relates to an oil sensor system and methods of using the same to determine the quality and condition of an oil and more particularly determining the presence of two-stroke or four-stroke engine oil, or the occurrence of an engine malfunction, such as a leak of antifreeze into the oil.

BACKGROUND

An oil's usable life may vary considerably, depending on many factors, such as oil quality, engine type and condition, ambient conditions, and vehicle service schedule. Currently, automobile manufacturers recommend oil-change intervals for gasoline-engine-powered cars and light-duty trucks of either 3 months/3000 miles or 12 months/7500 miles, depending primarily on the vehicle driving cycle and ambient conditions. The use of the proper quality (i.e., SG/CD) engine oil is assumed in recommending these intervals.

Several problems exist with the current method of specifying oil-change intervals:

(1) The vehicle's Owners Manual is seldom read and is hard to understand.
(2) Most drivers do not fit nearly into either of the two discrete intervals recommended. Many should probably change oil somewhere between 3 months/3000 miles and 12 months/7500 miles.
(3) No provision is made for the use of the wrong quality oil.
(4) No provision is made for the occurrence of engine malfunctions, such as glycol leakage, which could reduce effective oil life.

A variety of oil sensor systems are known. One system is a computer algorithm, assuming "normal" engine function and the proper quality and amount of oil in the reservoir. That system calculates effective oil life based on oil temperature histogram, which is a function of both service schedule and ambient conditions. That system overcomes the first problem by telling the driver when to change the oil, minimizing the need for understanding the recommendations in the Owner's Manual. That system also overcomes the second problem by computing oil-change intervals which are appropriate for each individual's driving schedule. However, it does not address the third or fourth problems, as it has no means of detecting oil of the wrong quality or oil overstressed due to abnormal engine operating conditions.

A device which could measure certain key physical and/or chemical characteristics of an oil in an operating engine should theoretically overcome the remaining two problems discussed above. Such a system could be used either instead of, or in conjunction with, the oil-change indicator device described above. The advantages of an oil condition sensor are that it will signal the need for an oil change when the oil's conditions warrants it; reducing the possibility for costly engine repairs due to too infrequent changes, and, conversely, eliminating the wasting of oil due to the performance of unnecessary maintenance.

SUMMARY OF THE INVENTION

The invention includes an oil sensor system having an oil sensor including two spaced apart electrodes, a triangular waveform means, a comparison means and a signal means. The oil sensor system is used in situ (i.e., used directly in the engine) to determined the presence of two-stroke or four-stroke oil, or the occurrence of an engine malfunction, such as a leak of antifreeze into the oil.

The invention includes the method of positioning two spaced apart electrodes (could be interdigitated) in an engine to contact the oil to be tested. A triangular waveform is applied to the electrodes having maximum and minimum potentials of, for example, 5V and −5V, respectively. The output current is compared to predetermined values. For example: If the output current is below a threshold level, two-stroke oil is present. The threshold is proportion to the surface area of the electrodes and inversely proportional to the distance between the electrodes. The threshold is also proportional to the peak potential between the electrodes with a 5V potential being preferred and the frequency of the triangular waveform. By way of example, a sensor having an electrode surface area of about 0.785 in$^2$ and the electrodes positioned 0.006 inches apart, with a peak potential of about 5V, the output current (after being converted to voltage by a 1M$\Omega$ resistor) ranges from 1.8V to 3.4V at 50° C. when four-stroke oil is present. Under the same conditions and output current less than 0.5V represent that two-stroke engine oil is present. The sensor can also be used to determine the presence of glycol based on a threshold output current as an indication of engine malfunction. By way of example, a sensor having an electrode surface area of about 0.196 in$^2$ and electrode position 0.002 inches apart, with a peak potential of about 5V, will have an output current of about 7 $\mu$A or greater at 23° C. when the oil has been contaminated with 60 ppm glycol or more.

DETAILED DESCRIPTION

Because oils of the currently-recommended American Petroleum Institute (API) service classifications (SG/CD) contain polar additives, and because polar species are often produced in or introduced into engine oil during use, it is reasonably to assume that the electrochemical reactivity of an oil could change with use. It is this premise on which this device is based.

The device is composed of two inert metal plated iron electrodes, for example gold plated, with smooth surfaces (1 inch in diameter), and the gap between the two electrodes is filled up with test engine oil. Since the electrical conductivity of engine oil, in general, is extremely low (1), the two electrodes have to be closely spaced to lower the ohmic resistance. In this device, this distance was set at 0.015 cm.

Figure 1:
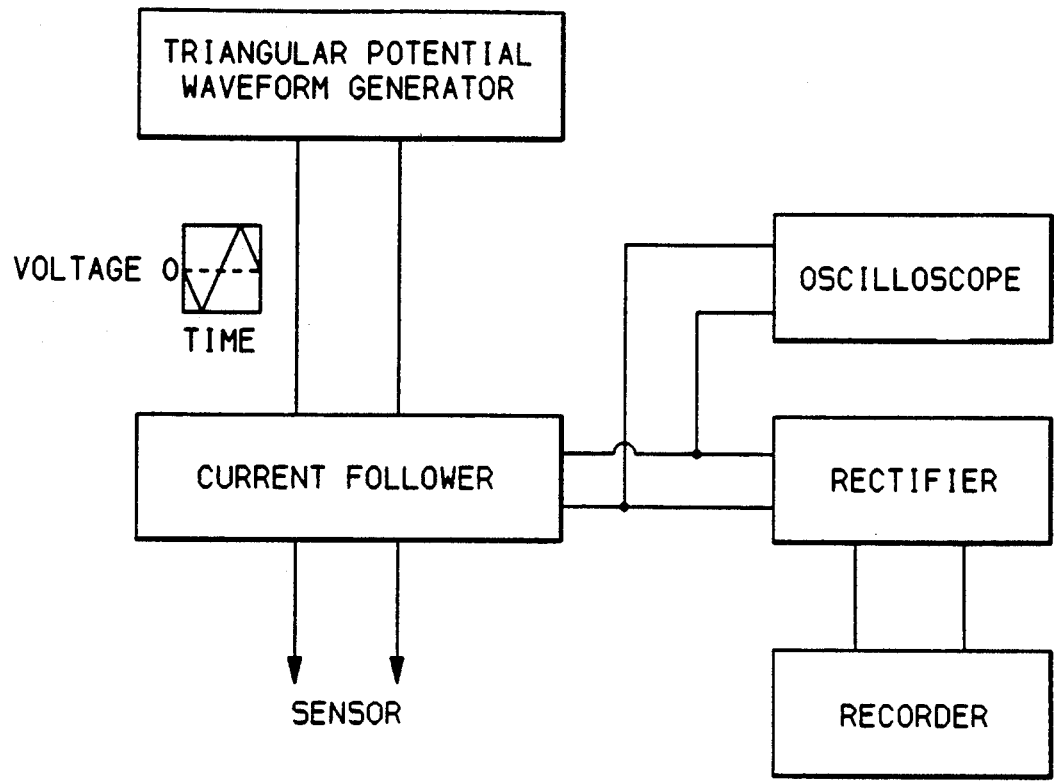
FIG. 1 is a schematic diagram of the operation of an oil sensor system according to the present invention.

A triangular waveform, produced by a Princeton Applied Research (PAR), Model 175 Universal Programmer, and a PAR Model 173 Potentiostat/Galvanostat, was applied between the two electrodes. To better match the standard TTL (transistor-transistor logic) circuit (in which 5V power supply is a standard), the maximum and minimum potentials of the triangular waveform were 5V and −5V, respectively. Fast scans (400 V/sec) were employed to increase measurement sensitivity (1). The current (or voltage) induced by the externally applied potential would thus be a measure of the electrochemical reactivity of the oil. With the external power supply peak-to-peak voltage at ±5V, the sensitivity of the sensor is limited by the spacing between the two electrodes. It is desirable to have the spacing smaller than 500 μm, so that the induced current exceeds 10 nA at room temperature. In order to further improve the sensitivity, the sensor operating temperature could be increased to 50° and 100° C. The block diagram is shown in FIG. 1, and the theory of this technique is described in the next Section.

THEORY

In this technique (1-2), a triangular potential waveform with a constant scan rate, dV/dt, (FIG. 1) is applied between two electrodes immersed in a test lubricant. As schematically illustrated in FIG. 1, the systems used for the oil sensor operates by sensing the concentration of electrochemically reactive material existing in the oil (or sensing the electrochemical reactivity of the oil).

A sensor may produce a response with and without an electrochemical reaction. When two electrodes are joined by a dielectric material, such as a lubricant, a capacitor is formed. Thus, the current response to this applied triangular waveform can be divided into two categories: (a) the current needed to charge the capacitor, $C * (dV/dt)$ (1), where C is the differential capacitance of the lubricant and (b) the current associated with electrochemical reactions occurring on the electrodes, $i_e$. The total current can then be expressed as:

$$i = C * (dV/dt) + i_e \quad (1)$$

Since both the scan rate and the capacitance C for a given lubricant are constants, the absolute value of $C * (dV/dt)$ is also a constant. If there is no electrochemical reaction occurring at the metal-lubricant interfaces, i.e., $i_e = O$, then Equation (1) reduces to, $$i = C * (dV/dt) \quad (2)$$

Figure 2A:
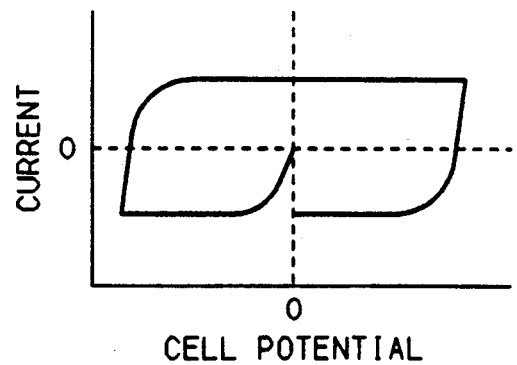
FIG. 2a is an illustration in graphic form of the current output verses cell potential of an oil sensor system according to the present invention when no electrochemical occurs at the electrodes.

Therefore, the absolute value of i is a constant. Under this condition, the voltammogram is rectangular (FIG. 2a).

Figure 2B:
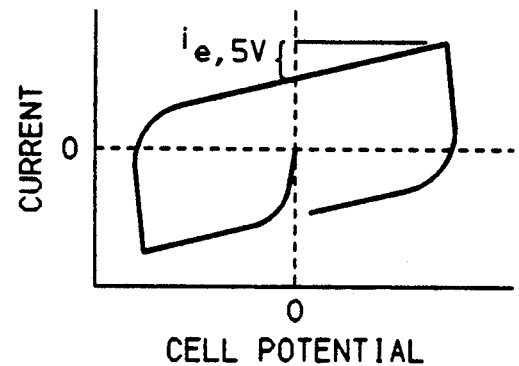
FIG. 2b is an illustration in graphic form of the current output verses cell potential of an oil sensor system according to the present invention when there is an electrochemical reaction at the electrode.

If electrochemical reactions occur at the metal-lubricant interfaces, then $i_e$ is no longer zero. A voltammogram obtained under this condition is shown in FIG. 2b. The electrochemical current $i_e$ at an applied voltage of 5V can be expressed as, $$i_{e,5V} = i_{5V} - C * (dV/dt) \quad (3)$$

where $i_{e,5V}$ and $i_{5V}$ are the electrochemical and the total current at 5V, respectively.

It is known that no electrochemical reaction occurs at the open circuit potential (i.e., 0V) thus, $$i_{0V} = C * (dV/dt) \quad (4)$$

Combining Equations (3) and (4), $i_{e,5V}$ can be calculated as, $$i_{e,5V} = i_{5V} - i_{0V} \quad (5)$$

Thus, the parameter, $i_{e,5V}$, can be estimated graphically from the cyclic voltammogram shown in FIG. 2b. This parameter is used as a measure of the electrochemical reactivity of lubricants. This parameter can be monitored using an oscilloscope. Alternatively, the cyclic voltammogram can be first converted to a potential waveform and then rectified to a DC output and recorded (see FIG. 1).

Figure 3:
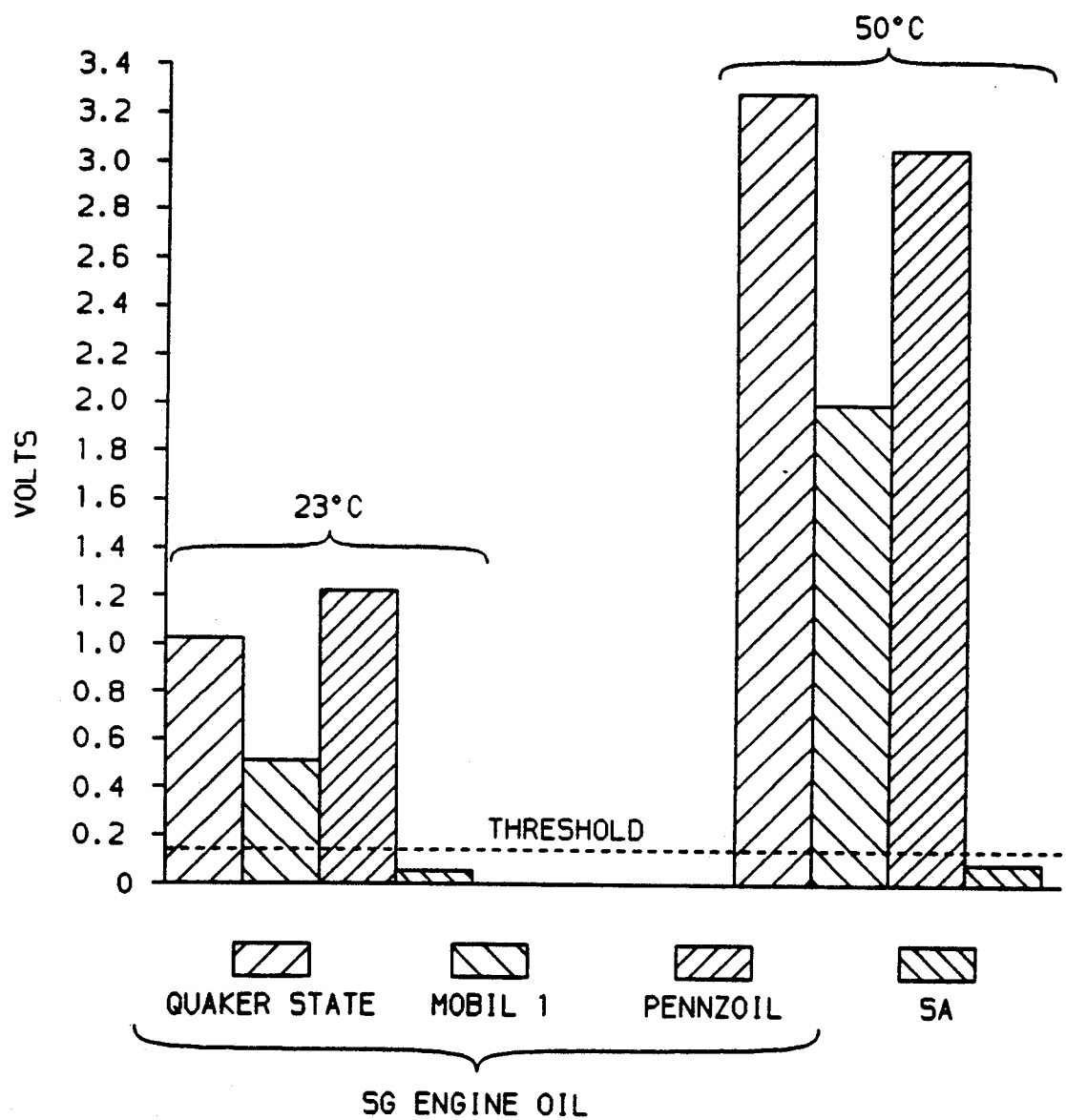
FIG. 3 is a block graph illustrating the output in volts of a sensor system according to the present invention for various brands (four-stroke engine oil) and types of oils tested at 23° C. and 50° C.

Currently, SG engine oils are recommended by automotive manufacturers. Although SA-type oils (base stocks) are not recommended by manufacturers, they are commercially available. The use of SA-type oils could damage engine parts in a short period. We have found that detergent is the key additive contributing to the electrochemical reactivity of fresh engine oil. Since SA-type oils do not contain detergent, the reactivity of SA-type oils is extremely low. Therefore, the sensor output obtained from a SA-type oil is much lower than those from SG oils at both room temperature (23° C.) and 50° C. (FIG. 3). The use of a "wrong" oil can thus be easily detected by setting a threshold voltage (FIG. 3). If the initial voltage reading obtained is lower than the threshold voltage, then (by methods known in the art) a signal can be sent causing a warning light, such as on a dashboard, for the wrong engine oil to turn on. This warning system can help engines from being damaged.

Figure 4:
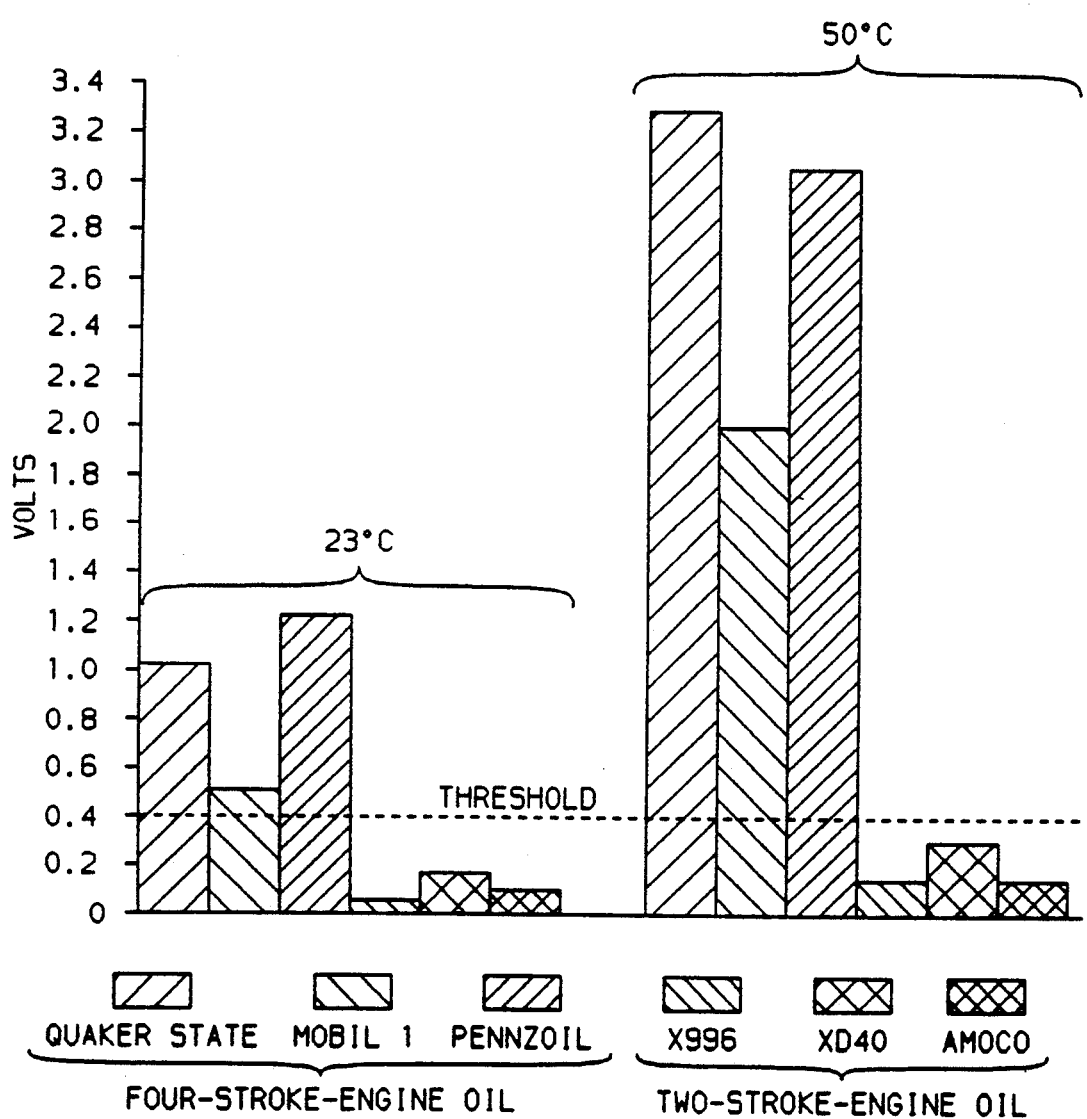
FIG. 4 is a block graph illustrating the output in volts of a sensor system according to the present invention for two-stroke and four-stroke oils.

Automobile manufacturers are interested in developing two-stroke-cycle engines because of their higher efficiency, lower pollution level, and more compact size as compared to four-stroke engines. However, if four-stroke-engine oil is added to the oil reservoir on a two-stroke-engine car by mistake, the catalytical converter could be severely poisoned. This is because metal elements contained in the four-stroke-engine oils could be reduced and coated on the active sites of the catalytical converter. Use of four-stroke oil on two-stroke engines can also cause engine damage due to sticking rings, and deposit formation inside the engine. Therefore, a sensor which can distinguish two-stroke-engine oils from four-stroke-engine oils are needed. The electrochemical reactivity of two-stroke-engine oils is very low because the additives in two-stroke-engine oils are electrochemically inactive and low in quantity. Therefore, the sensor outputs obtained from two-stroke-engine oils are much lower than those from SG oils at both room temperature and 50° C. (FIG. 4) Again, the use of "wrong" oil can easily be detected by setting a threshold voltage output from the oil sensor (FIG. 4).

Figure 5A:
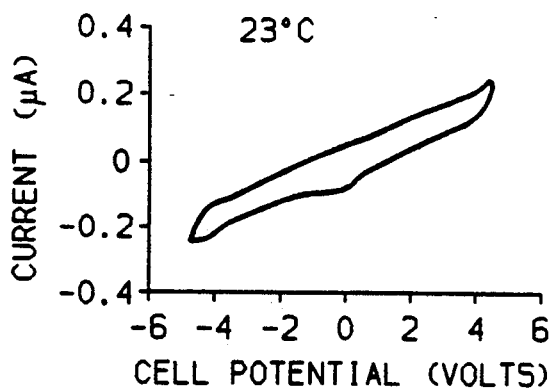
FIG. 5a is an illustration in graphic form of the current output verses cell potential of an oil sensor system according to the present invention for fresh engine oil at 23° C.
Figure 5B:
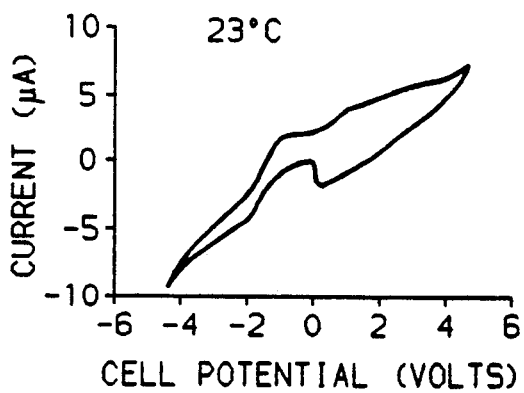
FIG. 5b is an illustration in graphic form of the current output verses cell potential of an oil sensor system according to the present invention for engine oil with 60 ppm glycol at 23° C.

Another problem that exists with the current method of specifying oil-change intervals is that no provision is made to account for the occurrence of engine malfunction, such as a leak of antifreeze (an ethylene glycol-water mixture) into the oil. Even a few hundred ppm of glycol can cause detrimental changes in engine oil, e.g., heavy sludge deposits, hydrolysis of the zinc dialkyldithiophosphate antiwear additive, and hastening of the degradation of the engine oil. Since the reactivity of glycol is at least one order of magnitude higher than that of SG engine oils, glycol leakage can be detected by this sensor. A typical cyclic voltammogram of fresh, uncontaminated engine oil at room temperature is shown in FIG. 5a. After the addition of 60 ppm of glycol, the measured current increased drastically, as shown in the cyclic voltammogram in FIG. 5b. Good correlation ($r^2 > 0.97$) was established between the measured current and the concentration of glycol in the engine oil.

Figure 6:
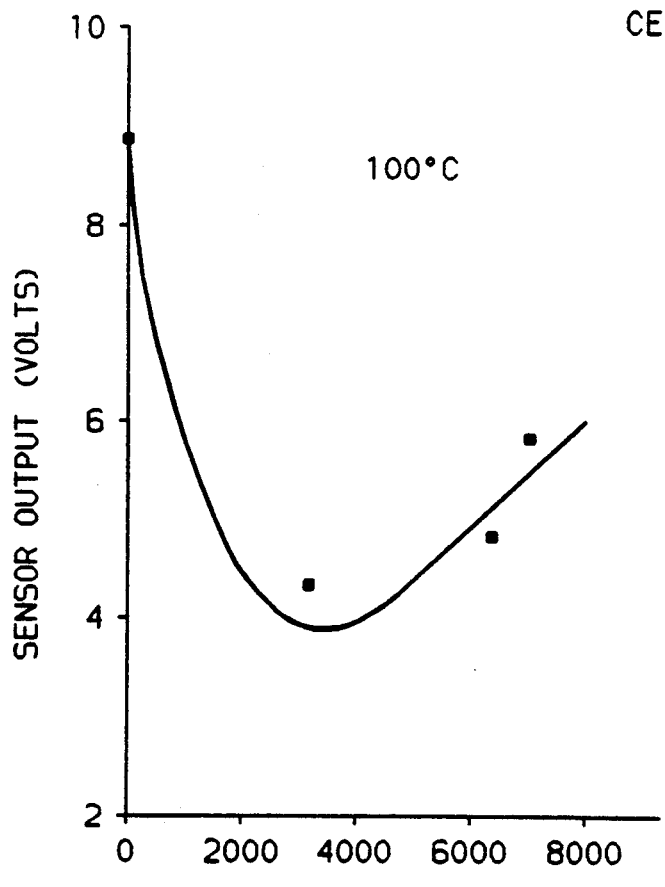
FIG. 6 is an illustration of output in volts of an oil sensor system according to the present invention as a function of miles driven of an automobile having an oil lubricated engine.

When the sensor was tested in the oil samples collected from a road test, it is seen that the output current first declined abruptly and then increased gradually as the engine oil aged or degraded (see FIG. 6). The decrease of the current is due to the consumption of detergent. Since an oil's acid number will increase with use, the current increase could be associated with an electrochemical reaction involving the acidic decomposition products of engine oil. Therefore, provided with the history of the oil usages, this sensor can also be used to monitor the oil condition and signal the need of an oil change.

Figure 7:
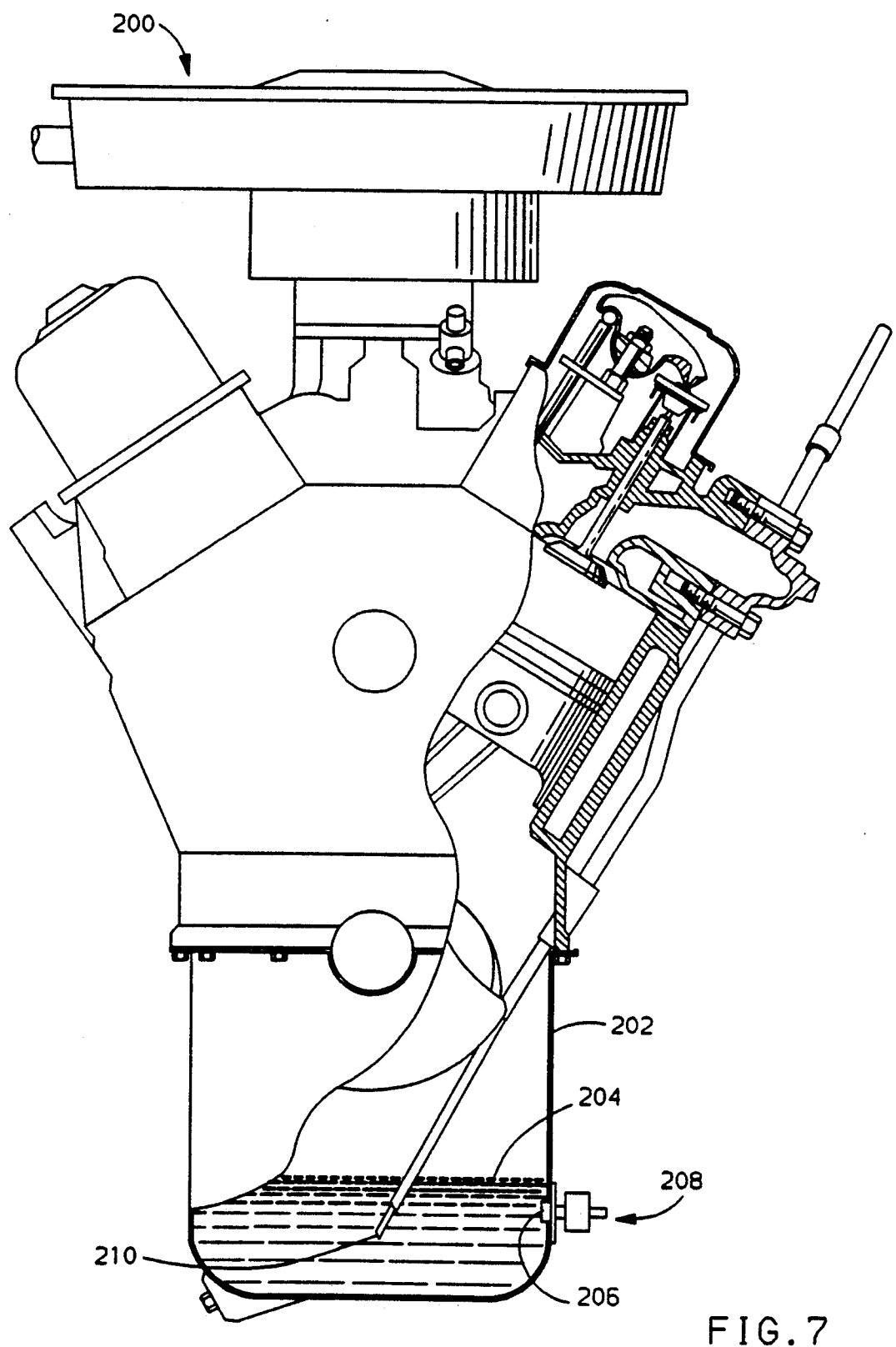
FIG. 7 is an illustration of an automotive engine having an oil sensor located in an oil passage of the engine according to the present invention.

FIG. 7 shows an engine 200 having an oil reservoir 202 containing oil 204. The engine may be two-stroke or four-stroke. The oil sensor 206 may be positioned in any oil passage in the engine or with the oil filter which would provide sufficient contact with the oil to allow the sensor to measure the oil. As shown in FIG. 7, the sensor 206 may be attached to the inside wall of the oil reservoir below the oil level and connected to a power source 208 in a manner known in the art. Another preferably position for the sensor is at the tip of the oil dipstick 210. The sensor is also connected to a means (not shown) for applying a triangular waveform potential to the electrodes as described, to a means (not shown) for measuring the change in current between the electrodes, a means (not shown) for comparing the measured current change between electrodes with predetermined values corresponding to two-stroke oil, four-stroke oil and oil including antifreeze, and a signal means (not shown) for sending a signal to a display means or recording means (not shown) in a manner determined as a function of the comparisons.

The embodiments of the invention in which an exclusive property or privilege is claimed are defined as follows:

1. A method of determining the quality of an oil comprising:
    placing two spaced apart electrodes in an oil to be tested;
    applying an alternating current triangular waveform potential to the electrodes;
    measuring the electrochemical current, being the induced current minus the capacitance component current, between electrodes; and
    comparing the measured electrochemical current with predetermined values corresponding to two-stroke oil, four-stroke oil and oil including antifreeze.

2. An oil sensor system comprising:
    two spaced apart electrodes;
    a means for applying a triangular waveform potential to said electrodes;
    a measuring means for measuring the electrochemical current, being the induced current minus the capacitance component current, between said electrodes;
    a comparison means for comparing the measured electrochemical current with predetermined values corresponding to two-stroke oil, four-stroke oil and oil including antifreeze; and
    a signal means for sending a display signal in a manner determined as a function of the comparison.

3. An oil sensor system as set forth in claim 2 wherein said means for applying an alternating current potential applies a maximum of 5V and a minimum of −5V.

4. An oil sensor system as set forth in claim 3 wherein the predetermined value corresponding to two-stroke oil is less than 0.4V at 50° C.

5. An oil sensor system as set forth in claim 3 wherein the predetermined value corresponding to four-stroke oil range from about 1.8 to about 3.4V at 50° C.

6. An oil sensor system as set forth in claim 3 wherein the predetermined value corresponding to oil including antifreeze is greater than 2V at 23° C.

7. A method as set forth in claim 1 wherein the applied potential as a constant rate.

8. A method as set forth in claim 1 wherein said potential has a maximum of 5V and a minimum of −5V.

9. A method as set forth in claim 8 wherein said constant rate is about 400V/sec.

10. A device comprising:
    an engine;
    an oil reservoir;
    two spaced apart electrodes positioned to contact oil used in the engine;
    a means for applying a triangular waveform potential to the electrodes;
    a measuring means for measuring the electrochemical current, being the induced current minus the capacitance component current, between the electrodes;
    a comparison means for comparing the measured electrochemical current with predetermined values corresponding to two-stroke oil and four-stroke oil; and
    a signal means for sending a signal as a function of the comparison.

11. A device as set forth in claim 10 wherein the predetermined value corresponding to the two-stroke oil is less than 0.4V at 50° C., and the predetermined value corresponding to four-stroke oil ranges from about 1.8V to about 3.4V at 50° C.

12. A device as set forth in claim 10 wherein the engine is a two-stroke engine.

13. A device as set forth in claim 12 wherein the electrodes are positioned in an oil reservoir to contact two-stroke combustion oil in the reservoir.

14. A device as set forth in claim 11 wherein the engine is a four-stroke engine.

* * * * *